United States Patent
Anderson et al.

(10) Patent No.: US 6,290,993 B1
(45) Date of Patent: Sep. 18, 2001

(54) COMPOSITIONS CONTAINING MIMOSA PHENOLIC COMPOUNDS

(75) Inventors: Jon Anderson, Hauppauge, NY (US); Lieve Declercq, Ekeren (BE); Donald F. Collins, Plainview; Thomas Mammone, Farmingdale, both of NY (US); Lieve Declerq, Ekeren; Hugo A. L. Corstjens, Maaseik, both of (BE)

(73) Assignee: E-L Management Corp., New York, NY (US)

( * ) Notice: Subject to any disclaimer, the term of this patent is extended or adjusted under 35 U.S.C. 154(b) by 0 days.

(21) Appl. No.: 09/360,884

(22) Filed: Jul. 23, 1999

(51) Int. Cl.[7] .......................... A61K 35/78; A61K 31/05; A61K 7/00
(52) U.S. Cl. .......................... 424/725; 514/731; 424/401
(58) Field of Search ................................ 424/195.1, 725, 424/401; 514/731

(56) References Cited

U.S. PATENT DOCUMENTS

| | | |
|---|---|---|
| 4,668,516 | 5/1987 | Duraffourd . |
| 5,122,374 | 6/1992 | De Guitaard et al. . |
| 5,700,468 | * 12/1997 | Bombardelli et al. . |
| 5,905,265 | * 5/1999 | Gubernick et al. . |

FOREIGN PATENT DOCUMENTS

| | | |
|---|---|---|
| 0 321 709 | 6/1989 | (EP) . |
| 0329834 | 8/1989 | (EP) . |
| 2578422 | 9/1986 | (FR) . |
| 2646602 | 11/1990 | (FR) . |
| 2710533 | 4/1995 | (FR) . |
| 6183940 | 7/1994 | (JP) . |
| 6183941 | 7/1994 | (JP) . |
| 8245359 | 9/1996 | (JP) . |
| WO 98/16188 | * 4/1998 | (WO) . |

OTHER PUBLICATIONS

Anton, et al., "Pharmacognosy of Mimosa Tenuiflora (Willd.) Poiret", Journal of Ethnopharmacology, 38: pp. 153–157, Elsevier Scientific Publishers Ireland Ltd., (1993).
Snook, et al., "The Flower Flavonols of Nicotiana Species", Photochemistry, vol. 31, No. 5, pp. 1639–1647 (1992).
Cronje, et al., "Oligomeric Flavanoids. Part 16. Novel Prorobinetinidins and the First A–Type Proanthocyanidin with a 5–Deoxy A–and a 3,4–cis C–Ring from the Maiden Investigation of Commercial Wattle Bark Extract", J. Chem. Soc. Perkin Trans., 1: pp. 2467–2477, (1993).
Snook, et al., "New C–4"–Hydroxy Derivatives of Maysin and 3'–Methoxymaysin Isolated from Corn Silks (Zea mays)", J. Agric. Food Chem., 43: pp. 2740–2745, (1995).
J. Chopin, "Synthesis of C–Glycoflavonoids", Acta Physica et Chimica, 18: pp. 273–284, (1971).
Englert, et al., "C–Glycosylflavones from Aerial Parts of Mimosa Pudica", Phytochemical Notes, 60: p. 194, (1993).
Kumazawa, et al., "Practical Synthesis of a C–Glycosyl Flavonoid via O→C Glycoside Rearrangement", Bull. Chem. Soc. Jpn., 68: No. 5, pp. 1379–1384, (1995).

* cited by examiner

Primary Examiner—Francisco Prats
Assistant Examiner—Susan D. Coe
(74) Attorney, Agent, or Firm—Karen A. Lowney, Esq.

(57) ABSTRACT

The invention relates to topical cosmetic and pharmaceutical composition for enhancing collagen levels in skin cells, the compositions comprising an effective amount of a biologically active phenolic compound-containing extract, or active fraction thereof, obtainable from *Mimosa pudica*.

15 Claims, No Drawings

COMPOSITIONS CONTAINING MIMOSA PHENOLIC COMPOUNDS

FIELD OF THE INVENTION

The present invention relates to topical cosmetic or pharmaceutical compositions. More specifically, the invention relates to cosmetic compositions containing compounds obtainable from *Mimosa pudica*, the compositions being useful in maintaining and/or increasing collagen levels in the skin.

BACKGROUND OF THE INVENTION

Plants of the genus Mimosa are well-known and widespread throughout the tropical and subtropical regions of the world. Extracts of certain members of this genus, as well as the related genus Acacia, are known to have certain biological activities, for example, as an antispasmodic, astringent, antidiarrheal, and antirheumatic. Particularly well known in the species *Mimosa tenuiflora*, a shrub the bark of which has been used in the treatment of burns and the prevention of inflammation (Anton et al., *J. Ethnopharmacol.* 38: 153–157, 1993; FR 2710533). Other activities attributed to extracts of this plant include epidermal regeneration,(U.S. Pat. No. 5,122,374; EP 321709), enhancement of activity of alpha-acetoxy acids (FR 2646602), and antipruritic (FR 2710533). More specific analysis of the activity of *M. tenuiflora* has identified the activity of this extract as being due to triterpenoid saponins (Anton et al., supra).

A less well-known species of Mimosa is *M. pudica*. To date, although its chemistry has been studied to some extent (Englert et al., *Planta Med.* 60:,194, 1993), any proposed biological activity has been based on rooted primarily in ethnic medicine; suggested activities include a remedy for sleeplessness, spasms and convulsions of children. It has now been unexpectedly discovered that *M. pudica* extracts exhibit useful anti-collagenase activity, which activity is based on a different class of compounds than those identified as actives in *M. tenuiflora*.

SUMMARY OF THE INVENTION

The present invention relates to topical cosmetic and pharmaceutical compositions comprising an effective amount of a biologically active phenolic compound-containing extract, or active fraction thereof, obtainable from *Mimosa pudica*. Such compositions are useful in the maintenance and enhancement of collagen levels in the skin, and as such are useful in methods of preventing or treating fine lines and wrinkles, as well as preventing or treating the loss of skin firmness or elasticity, which are associated with chrono- and photoaging. In a preferred embodiment, the composition contains at least one Mimosa pudica flavonoid, more preferably, at least C-glycosyl flavonoids, or a derivative thereof.

DETAILED DESCRIPTION OF THE INVENTION

It has now been unexpectedly discovered that a phenol-containing extract of *Mimosa pudica* possesses strong biological activity, with the ability to maintain or enhance the levels of collagen in skin cells. More specifically, when provided to human fibroblasts, a phenolic-containing fraction of *M. pudica* can increase the collagen levels in these cells by as much as 100% or more, when provided at relatively low concentration. When the active extracts are treated to remove phenolics, the extract loses its activity.

The biologically active extracts of *M. pudica* useful in this invention can be prepared by any means capable of extracting phenolic compounds from the plant material, using standard extraction techniques. Such extractions include, but are not limited to, ethanol, methanol, ethyl acetate, acetone, chloroform and water, or any other solvent and water. (Englert et al., supra) The active phenolic fraction can be obtained from any portion of the plant, but preferably the extract is taken from the aerial portions of the plant, including leaves, twigs, stem, or bark, as well as seeds. The *M. pudica* phenolics useful in the present invention are preferably flavonoids, such as dihydrorobinetin, fustin, fisetinedol, robinetinedol, catechin, gallocatechin, or epigallocatechin, and derivatives thereof (see, e.g., Cronje et al., J. Chem. Soc. Perkin Trans. I: 2467–2477, or flavone aglycones, such as chysin, apigenin, luteolin, kaempferol, galangin, quercetin, rhamnetin, myricetin, gossypetin and the like. Most preferably, the compounds are C-glycosyl flavones and aglycones thereof. In one embodiment, the preferred compounds are maysin, ax-4"-OH-maysin, 2"-O-rhamnosylorientin, and 2"-O-rhamnosyl isoorientin and the aglycone luteolin.

It will be understood that in addition to direct use of an extract, it is also possible to use the phenolic compounds per se from whatever source they are obtainable. For example, C-glycosyl flavonoids are also obtainable and have been isolated from *Zea mays* (Snook et al., Photochemistry 31: 1639–1647, 1992; Snook et al., J. Agric. Food Chem. 43:2740–2475, 1995), as well as from *M. pudica* (Englert et al., supra). The compounds can also be made synthetically by known chemical reactions, as described, for example, in Chopin, Acta. Phys. Chim. Debrecina 17: 273–284, 1971, and Kumazawa et al. Bull. Chem. Soc. Japan 68: 1379–1384, 1995. The contents of each of the foregoing documents are incorporated herein by reference.

As used herein, what constitutes "an effective amount" of an extract, or an active portion thereof, will depend on the purity of the source. For example, if a crude phenolic-containing extract of about 20% purity is employed, the extract will normally be used at a level of about 0.01–10% by weight of the composition. On the other hand, the higher the level of purity, the smaller the percentage required to achieve the same effect. Assuming a substantially pure phenolic extract (i.e., an extract containing at least about 90% active phenolics or flavonoids), the concentration range will be about 0.001 to about 5% by weight of the composition, preferably about 0.01 to about 3%, most preferably about 0.1 to about 1%.

The extract or substantially pure flavonoids or flavonoid aglycones can be delivered in any form appropriate for topical application. Such forms include solutions, colloidal dispersions, emulsions (oil-in-water or water-in-oil), suspensions, powders, creams, lotions, gels, foams, mousses, sprays and the like. Methodology for formulation of different vehicle types is well known in the art, and can be found for example in Remington's The Science and Practice of Pharmacy, 19th Edition, Volume II.

The compositions of the invention are useful in the prevention or treatment of any condition in which the activity of collagenase and/or the reduction of collagen levels in the skin are a factor. For example, the compositions can be used to reduce the appearance of fine lines and wrinkles on the skin, due to either chrono- or photoaging. In a similar vein, the compositions are also useful in improving the firmness and elasticity of aging skin. The compositions also have a number of therapeutic uses. One example is in the promotion of the process of wound healing. The compositions can also be used in the treatment of conditions such as scleroderma, and keloids. Another use is the treatment of collagen-related conditions induced by topical and systemic drugs, e.g. corticosteroids and retinoids. Topical corticosteroids are widely used for the treatment of inflammatory skin disorders, but the most common adverse effect is skin atrophy due to decreased collagen synthesis, and the present compositions can be used to treat or prevent the occurrence of atrophy.

The compositions can be applied directly to the skin in need of treatment in an amount of from about 0.1 $\mu g/cm^2$ to 2 $mg/cm^2$ of skin. For cosmetic purposes e.g., for treatment or prevention of the symptoms of chrono- or photoaging, it is preferable that application be performed from about once per week to about 4 or 5 times daily, preferably from about 3 times a week to about 3 times daily, most preferably about once or twice per day. By "chronic" application, it is meant herein that the period of topical application may be over the lifetime of the user, preferably for a period of at least about one month, more preferably from about three months to about twenty years, more preferably from about six months to about ten years, more preferably still from about one year to about five years, thereby resulting in the treatment or prevention of the external signs of aging. With regard to therapeutic uses, such as wound-healing, drug-induced skin-atrophy, keloids and other collagen-related skin conditions, it will ordinarily be necessary to apply the compositions, on an as-needed basis, for example, once or twice daily, until relief of the symptoms is achieved.

The following non-limiting examples illustrate the compositions and methods of the invention.

EXAMPLES

Unless otherwise specified, throughout the following examples, the Mimosa pudica extract employed is a crude extract with 70% ethanol, obtained from Serdex.

1. Collagen-Increasing Activity

Normal human dermal fibroblasts are seeded and grown to confluence in a 96-well plate prior to being treated with M. pudica extract or fractions thereof, prepared by solvent/solvent extractions (heptane/70% ethanol, ethyl acetate/water) at various concentrations in complete medium. Media alone serves as negative control and TGF-β serves as positive control. The plates are incubated for 4 days at 37° C./5% $CO_2$ before the supernatants are harvested and stored at −70° C. until an ELISA is performed. Antibodies to collagen type 1 or procollagen type 1 are used for ELISA analysis to determine collagen levels. The results show an increase of 100% in collagen levels using the crude extract at 50 ppm; 118%, 142%, and 166%, for more refined fractions of the extract at 50 ppm, compared with 46% increase with 5 ng/ml of TGF-β. This demonstrates the potent activity of M. pudica extracts in enhancing collagen levels.

2. Anti-Collagenase Activity

To elucidate the mechanism of the extracts effect, assays for collagenase inhibition (EnzChek™ Collagenase assay kit, Molecular Probes) are performed in a well-plate (total reaction volume is 200 μl). The assay is performed in reaction buffer, which consists of 0.05M Tris-HCl, 0.15M NaCl, 5 mM $CaCl_2$, 0.2 mM sodium azide at pH 7.6. Various M. pudica fractions are dissolved at increasing concentrations in reaction buffer, which may eventually contain small amounts of organic solvent to improve the solubility. To each assay well 80 μl of the M. pudica sample is added. Next, 20 μl of the collagenase substrate DQ qelatin (1 mq/ml in PBS) is added. Lastly, 100 μl of enzyme (*Clostridium histolyticum* collagenase, 0.6 U/ml in reaction buffer) is added. The fluorescence ($\lambda_{ex}$=485 nm; $\lambda_{em}$=530 nm) is measured for about 20 minutes (Luminescence Spectrometer LS 50B, Perkin Elmer). The $IC_{50}$ value for the *M. pudica* extract, which is estimated from the initial reaction velocity for each assay well, is about 75 μg/ml.

Subsequent testing of various fractions of the extract, and precipitates from the partitioning, continue to show strong activity against collagenase. However, when active samples are filtered through a polyamide column (PVP) to remove phenolics, the activity is eliminated, indicating that the active component(s) is a phenolic compound.

3. Identification of Active Compounds

A crude extract from the aerial parts of *M. pudica* is obtained by partitioning a heptane degreased 70% ethanol extract between ethyl acetate and water. The nature of the anti-collagenase activity is already shown to be phenolic, as shown above. The ethyl acetate extract is subsequently partitioned between butanol and acidified (pH5) water, the butanol residue is taken up in methanol and precipitated with ether and then undergoes a two-step fractionation procedure using preparative HPLC. At each step the anti-collagenase activity is evaluated and the most active fraction selected for further refinement. Compounds found in the most active fraction are identified as maysin and ax-4"-OH maysin.

4. Effect of Extract on Skin

A clinical study is designed to observe the effect of mimosa extract on skin firmness, fine lines and wrinkles, and skin thickness. Three samples are prepared, one containing 0.2% of crude extract, a second containing 0.2% of a clarified portion of the extract, and a third with vehicle only. A total of 47 female volunteers are employed, of which 46 finished the study. The panelists are provided with a product to be applied around the eye area twice a day for 8 weeks. All panelists are allowed to continue to use cleansers, sunscreens and makeup products during the course of the study. Measurements are obtained before treatment, and after 4 weeks and 8 weeks.

At each time point, the panelists are allowed to equilibrate for 30 minutes before commencement. The following measurements are obtained: Fine lines and wrinkles, using silicone replicas obtained from the outer canthus area of both sides of the face at each visit; ultrasound imaging of the outer canthus area; skin firmness using a ballistometer.

The results indicate a 24% and 25% reduction, relative to baseline, in fine lines and skin wrinkles after 4 and 8 weeks respectively, with the extract. The clarified samples show a 26% and 30% reduction at 4 and 8 weeks, respectively. The vehicle is only 13% effective, a result possibly due to skin hydration.

Ultrasound indicates the most dense and least areas of the skin, presumed to be associated with higher concentrations of collagen and elastin. An improvement in skin density is reflected as an increase in the denser areas and decrease in the thinner areas. After 4 weeks, with the extract, there is a 16% increase in denser areas, and 30% increase after 8 weeks; with the clarified extract, the improvement is 33% and 37%, at 4 and 8 weeks respectively. The vehicle is only effective at 19% and 16%. Concurrently, thinner areas decrease by 15% and 14% with the extract, 21% and 18% with the clarified extract, and 15% and 7% with the vehicle.

Skin firmness measured by ballistometer increases with the extract by 8% and 22% at 4 and 8 weeks; with the clarified extract, the increase is 16% and 24%; and with the vehicle the increase is 7% and 8%.

All the foregoing results indicate a potent activity of *M. pudica* extracts in improving the various measured signs of aging.

What we claim is:

1. A method for treating or or reducing the appearance of fine lines and wrinkles on the skin comprising applying to the skin of a person in need thereof a composition comprising an effective amount of a biologically active phenolic compound-containing *Mimosa pudica* plant extract, or active fraction thereof.

2. The method of claim 1 in which the phenolic is a flavonoid or flavone aglycone.

3. The method of claim 1 in which the phenolic is a C-glycosyl flavonoid or an aglycone thereof.

4. The method of claim 1 in which the phenolic is maysin, ax-4"-OHmaysin, 2"-O-rhamnosylorientin, and 2"-O-rhamnosyl isoorientin, luteolin, or a combination thereof.

5. The method of claim 1 in which the composition comprises about 0.001 to about 10% of phenolic compound-containing extract or active fraction thereof.

6. A method of inhibiting collagenase activity in the skin comprising applying to the skin of a person in need thereof a composition comprising an effective amount of a biologically active phenolic compound-containing *Mimosa pudica* plant extract, or active fraction thereof.

7. The method of claim 6, in which the phenolic is a flavonoid or flavone aglycone.

8. The method of claim 6 in which the phenolic is a C-glycosyl flavonoid or an aglycone thereof.

9. The method of claim 6 in which the phenolic is maysin, ax-4"-OHmaysin, 2"-O-rhamnosylorientin, and 2"-O-rhamnosyl isoorientin, luteolin, or a combination thereof.

10. The method of claim 6 in which the composition comprises about 0.001 to about 10% of phenolic compound-containing extract or active fraction thereof.

11. A method of increasing skin firmness comprising applying to the skin of a person in need thereof a composition an effective amount of a biologically active phenolic compound-containing *Mimosa pudica* plant extract, or active fraction thereof.

12. The method of claim 11 comprising applying to the skin in which the phenolic is a flavonoid or flavone aglycone.

13. The method of claim 11 in which the phenolic is a C-glycosyl flavonoid or an aglycone thereof.

14. The method of claim 11 in which the phenolic is maysin, ax-4"-OH-maysin, 2"-O-rhamnosylorientin, and 2"-O-rhamnosyl isoorientin, luteolin, or a combination thereof.

15. A method of claim 11 in which the composition comprises about 0.001 to about 10% of phenolic compound-containing extract or active fraction thereof.

* * * * *

UNITED STATES PATENT AND TRADEMARK OFFICE
CERTIFICATE OF CORRECTION

PATENT NO. : 6,290,993 B1
DATED : September 18, 2001
INVENTOR(S) : Anderson et al.

It is certified that error appears in the above-identified patent and that said Letters Patent is hereby corrected as shown below:

<u>Title page,</u>
The inventors should appear as follows: Inventors: Jon Anderson, Hauppauge, NY; Neelam Muizzuiddin, Bethpage, NY; Donald F. Collins, Plainview, NY; Thomas Mammone, Farmingdale, NY, all of (US); Lieve Declerq, Ekeren; Hugo A. L. Cortjens, Maaseik, both of (BE)

Signed and Sealed this

Twenty-first Day of May, 2002

*Attest:*

*Attesting Officer*

JAMES E. ROGAN
*Director of the United States Patent and Trademark Office*